United States Patent [19]

Scribano et al.

[11] Patent Number: 4,658,207

[45] Date of Patent: * Apr. 14, 1987

[54] DEVICE FOR MEASURING THE WATER CONTENT OF INK SAMPLES

[75] Inventors: Gino A. Scribano, Willowbrook; Thomas A. Fadner, LaGrange, both of Ill.; Ira B. Goldberg, Thousand Oaks, Calif.

[73] Assignee: Rockwell International Corporation, El Segundo, Calif.

[*] Notice: The portion of the term of this patent subsequent to Dec. 17, 2002 has been disclaimed.

[21] Appl. No.: 717,050

[22] Filed: Mar. 28, 1985

[51] Int. Cl.⁴ .............................................. G01R 27/26
[52] U.S. Cl. ............................... 324/61 P; 324/61 QS; 73/61.1 R
[58] Field of Search ............... 324/61 P, 61 R, 61 QS; 73/61.1 R; 340/870.37, 620, 627; 361/433 A, 433 S

[56] References Cited

U.S. PATENT DOCUMENTS

| | | | |
|---|---|---|---|
| 2,593,766 | 4/1952 | Kimball et al. | 324/61 P |
| 2,759,147 | 8/1956 | Stein | 324/61 P |
| 4,114,090 | 9/1978 | Poskitt | 324/61 QS |
| 4,228,393 | 10/1980 | Pile | 324/61 QS X |
| 4,470,300 | 9/1984 | Kobayashi | 324/61 QS X |
| 4,559,493 | 12/1985 | Goldberg et al. | 324/61 R |

Primary Examiner—Reinhard J. Eisenzopf
Assistant Examiner—Jack B. Harvey
Attorney, Agent, or Firm—H. Fredrick Hamann; Craig O. Malin

[57] ABSTRACT

A device for measuring the water content in small samples of an ink-water mixture. The sample is used as the dielectric for a capacitor cell which includes inner and outer concentric electrodes. The ink sample fills a gap between the electrodes, thereby controlling the total capacitance of the cell. The cell is connected as part of an oscillator circuit, the output frequency of which varies in a known manner with the dielectric constant of the ink mixture, which in turn is determined by the mixture's water content. A display is provided which varies with the frequency of the output signal, thereby indicating the sample's water content. A mechanism is provided for conveniently removing the inner electrode so that a sample can be introduced, and then returning the inner electrode so that the sample floods the gap between the two electrodes. The ends of the electrodes are enclosed by conductive members to contain stray electric field, while thin, removable insulative liners are provided for the opposed electrode surfaces to impede electrolysis and double layer effects, and to facilitate cleaning.

11 Claims, 6 Drawing Figures

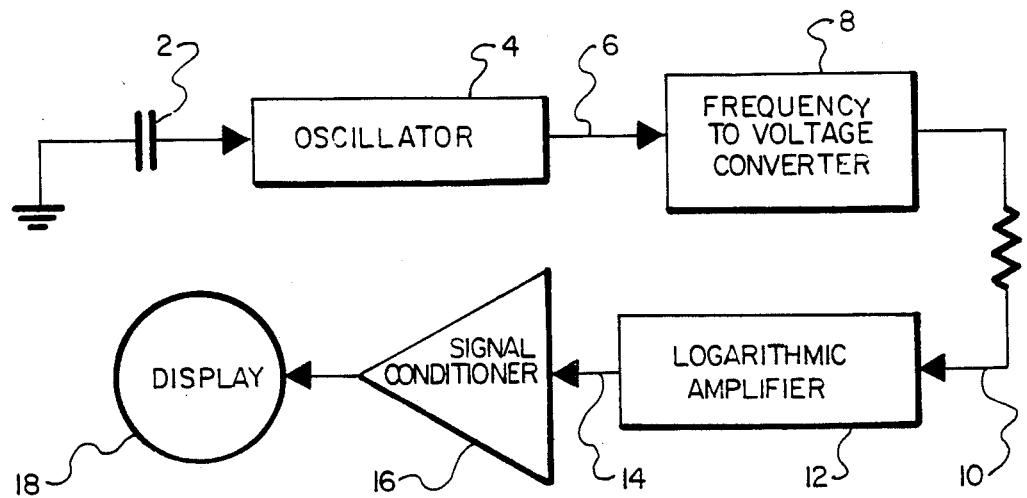
Fig.1.
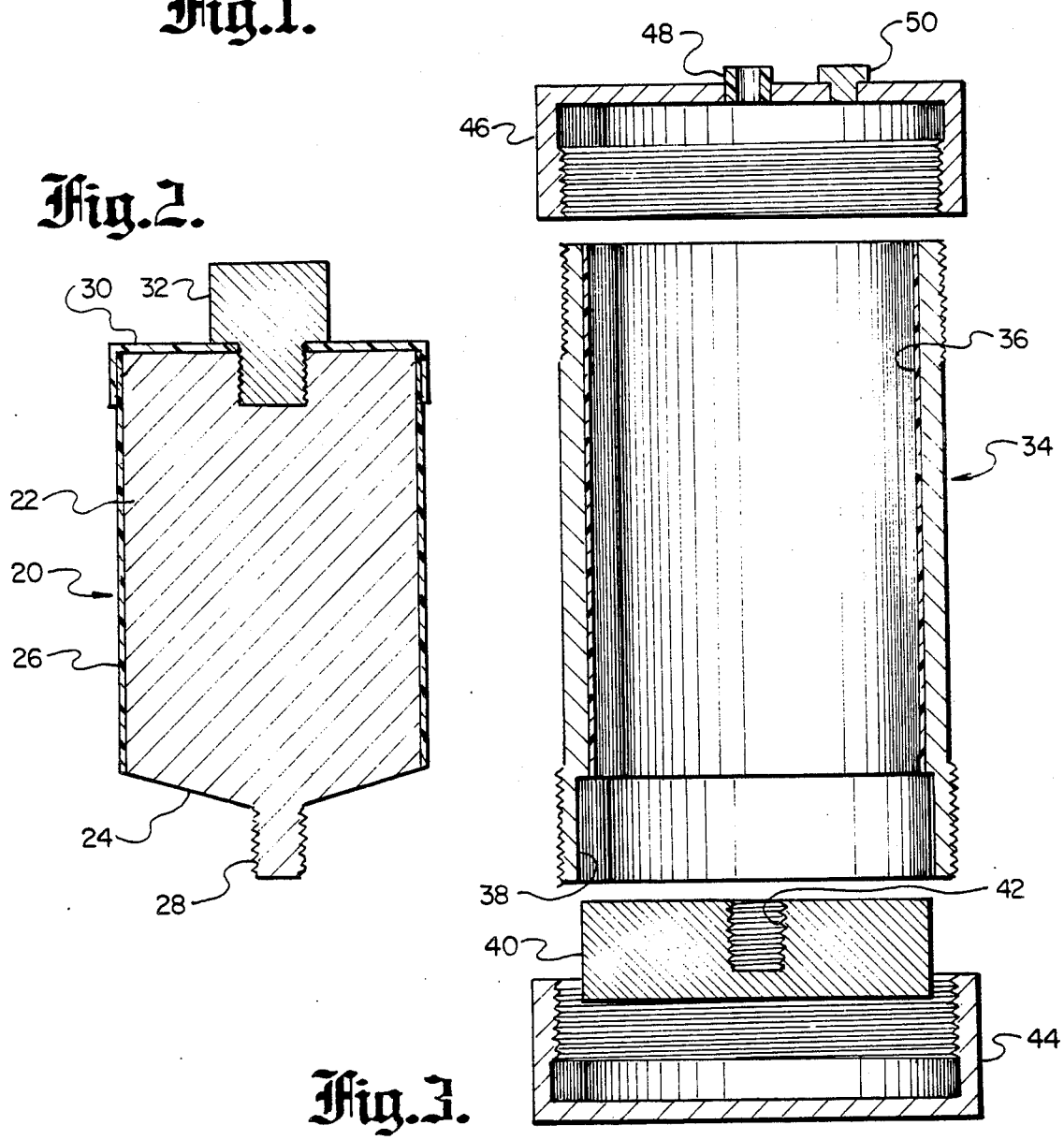
Fig.2.
Fig.3.

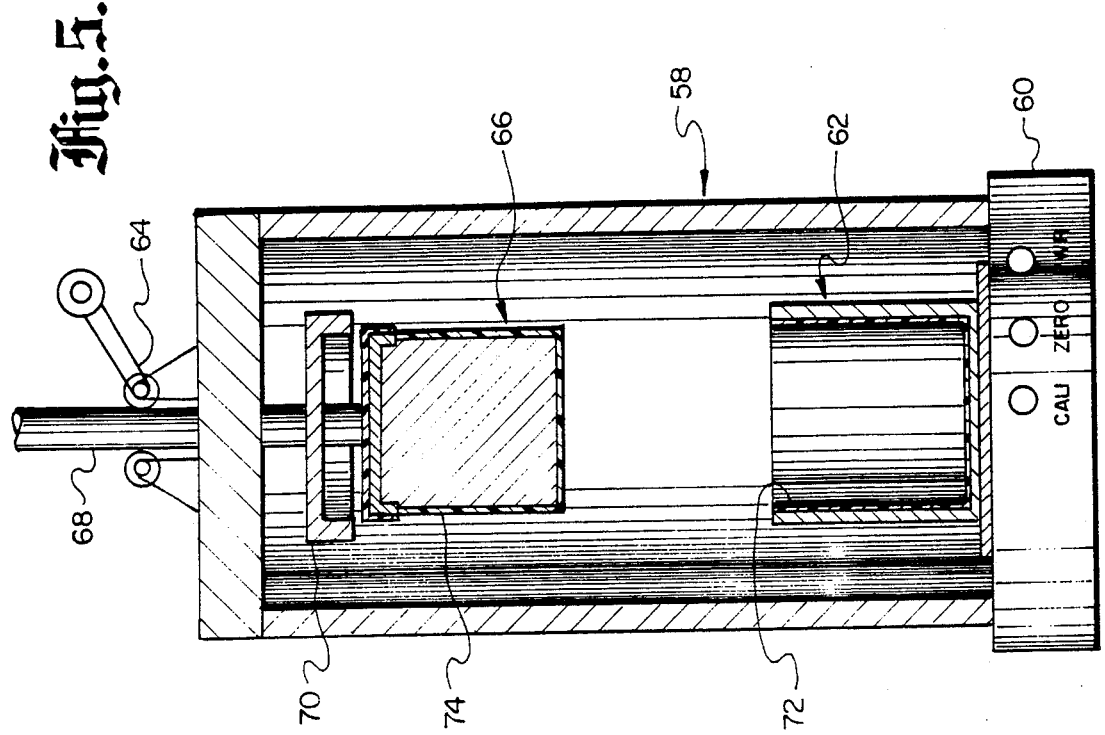
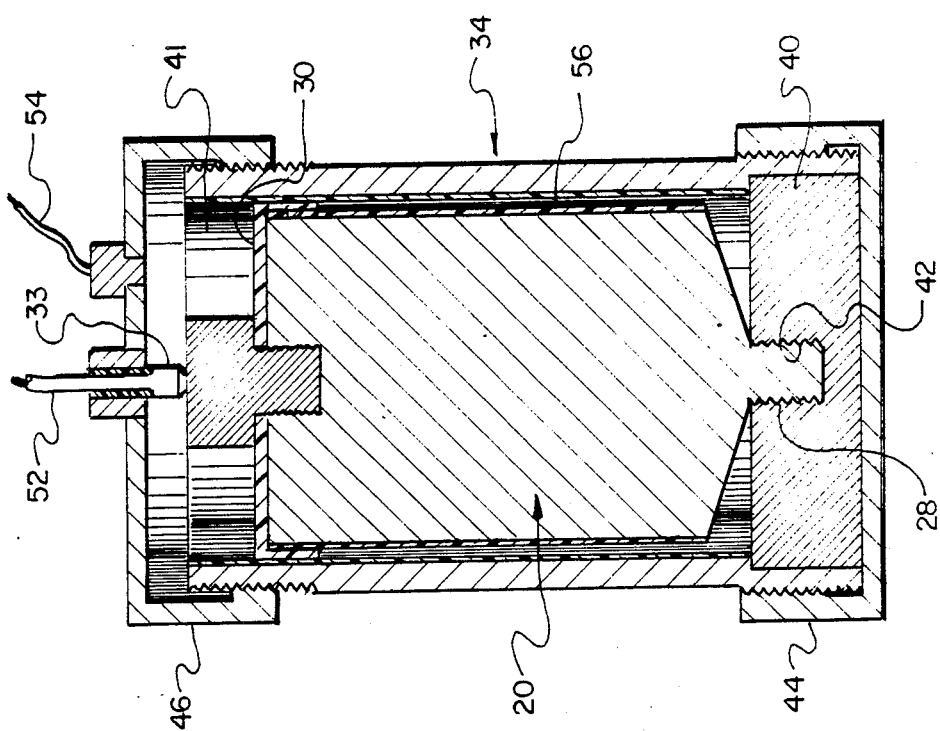

4,658,207

DEVICE FOR MEASURING THE WATER CONTENT OF INK SAMPLES

BACKGROUND OF THE INVENTION

This invention relates to fluid measuring devices, and more particularly to devices for measuring the concentration of water in a fluid mixture of ink and water, particularly mixtures of lithographic ink and water.

Better results are obtained from a printing press if the relative amounts of water or aqueous dampening solution and ink in the ink mixture are maintained at optimum levels. This can be accomplished at the beginning of a printing press operation by initially mixing the water or aqueous solution and ink in the proper proportions. However, over a period of time the proportions of ink and water in the recirculating ink mixture can change as printing progresses. Until recently, the printer attending the press had no means of automatically and continuously monitoring the concentration of water in a recirculating ink-water mixture. Rather, he had to rely upon his experience and examination of the printing results to estimate the dampening liquid concentration.

An automatic meter for measuring the concentration of water in an ink-water mixture is disclosed in U.S. patent application Ser. No. 616,106, filed June 1, 1984 by Goldberg et al. In this system an ink-water mixture flows through a capacitive sensing device which has the ability to detect changes in the dielectric constant of the mixture when used in conjunction with appropriate ciruitry. It is necessary to pump ink through the sensor of this system, and therefore relatively large quantities of ink are required. Because of this pumping and flow requirement, the sensor must be physically large to allow an easy flow of ink and still maintain a high electrical capacitance. It would be desirable to have a smaller, less complex and highly portable system which lends itself both to laboratory use and to rapid, multiple-position measurements at an ink manufacturing or printing plant.

SUMMARY OF THE INVENTION

In view of the above problems and limitations associated with the prior art, it is an object of the present invention to provide a novel and improved device for measuring the water or dampening liquid content of inks which is small in size, inexpensive and does not require peripheral equipment or attachments such as ink pumps or ink distribution systems.

Another object is the provision of a novel and improved device which is capable of measuring the water content of small, non-flowing ink samples, such as samples collected from printing press rollers while the press is running, or from various locations in the production run of an ink manufacturing plant.

These and other objects of the invention are accomplished in a measuring device which includes a specially designed, small scale capacitor cell having an ink sample as a dielectric. An oscillator circuit which includes the capacitor cell provides an output signal frequency that varies in a known manner with the dielectric constant of the sample ink, while an output means provides an output display that varies with the output signal frequency, and thereby indicates the concentration of water in the ink sample. The capacitor cell consists of a plurality of electrodes, each having appreciable surface areas, means for positioning the electrodes with their respective surfaces mutually opposed and separated by a predetermined gap, and means for containing a static ink sample in the gap between the electrodes. The amount of ink required to achieve a desired dielectric range is small, permitting the entire mechanism to be compact and portable.

In the preferred embodiment two generally cylindrical, coaxial electrodes are used, with the ink gap formed between the outer surface of the inner electrode and the inner surface of the outer electrode. A mechanism is provided to precisely position the inner electrode within the outer one so that repeatable measurements can be made. The inner electrode can be removed from the outer one for the introduction of an ink sample, and then replaced so that the ink is displaced into the gap between the two electrodes. Conductive caps are provided at either end of the electrodes to contain stray electric fields, while an insulative base contains the ink and prevents an electrical connection between the electrodes. Thin insulative layers are provided on the opposed electrode surfaces to impede electrolysis and double layer capacitive effects, and are preferably made removable to facilitate cleaning the measuring device. In one embodiment the inner electrode has an extension which is screwed into an insulative block at the bottom of the outer electrode, and conductive caps are threaded in place over the outer electrode. In another embodiment a frame assembly holds the outer electrode in place, while the inner electrode is raised and lowered into an operative position by means of a shaft on the electrode which is engage by a hoist mechanism on the frame assembly. Each embodiment is quite simple in constuction, and can be implemented as a small and easy to use device.

Other features and advantages of the invention will be apparent to those skilled in the art from the following detailed description of preferred embodiments, taken together with the accompanying drawings, in which:

DESCRIPTION OF THE DRAWINGS

FIG. 1 is a block diagram of a circuit used to measure the water content of static ink samples in accordance with the invention;

FIG. 2 is a sectional view of the inner electrode employed in the capacitive sample cell for one embodiment of the invention;

FIG. 3 is an exploded sectional view of the outer electrode and associated parts used in the same embodiment;

FIG. 4 is a sectional view of the inner and outer electrodes assembled in an operative capacitive cell;

FIG. 5 is a sectional view of another embodiment of the invention; and

DESCRIPTION OF THE PREFERRED EMBODIMENTS

Figure 6:
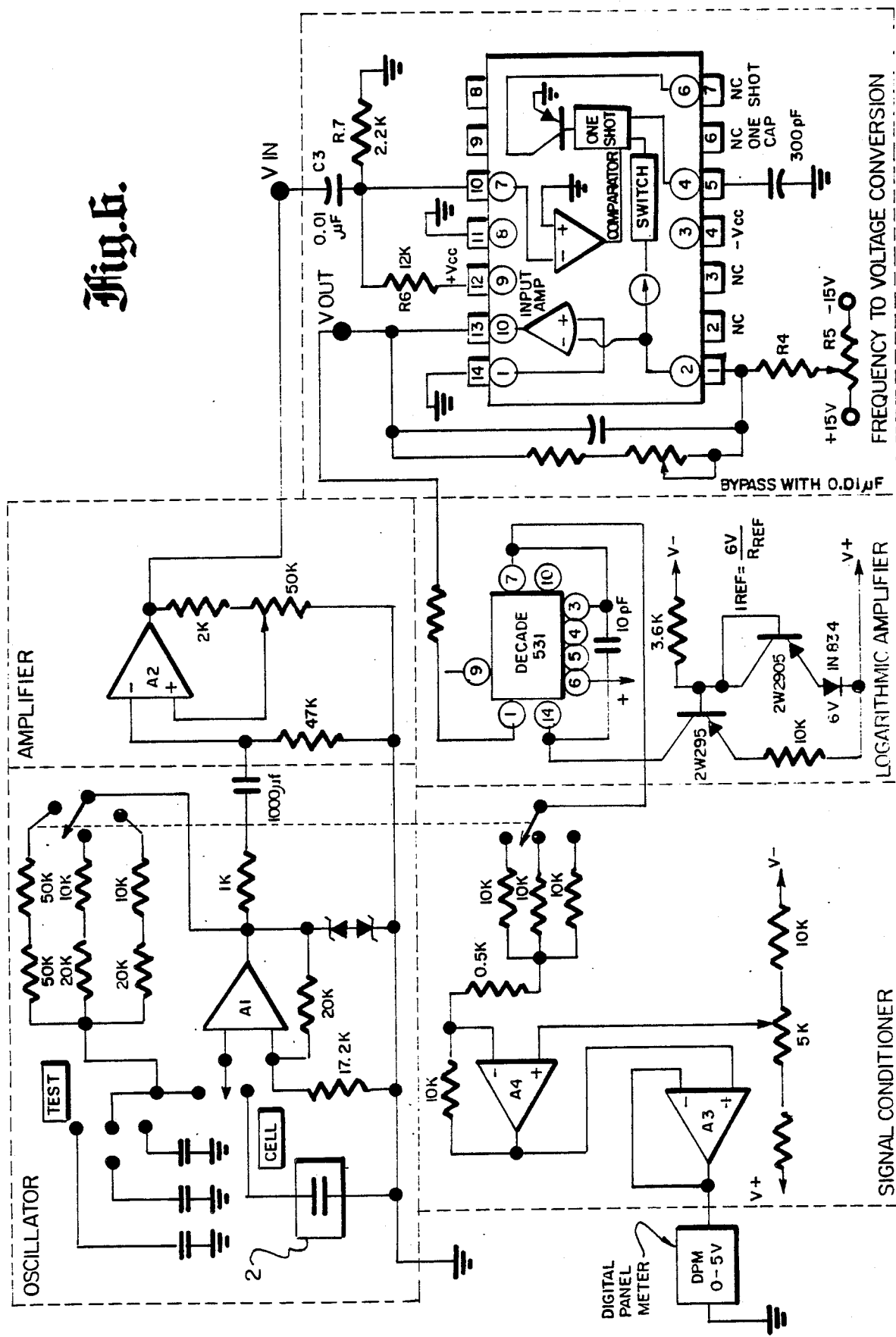
FIG. 6 is a schematic diagram of circuitry that may be used in conjunction with the invention.

As noted in the Goldberg et al application, Ser. No. 616,106, now U.S. Pat. No. 4,559,493, it has been discovered that, with respect to the concentration of water in an ink-water mixture, the logarithm of the real component of the dielectric constant is linear. It was further discovered that this relationship applied to many different types of lithographic ink, and that it had only a small temperature dependence.

A block diagram of a capacitive measurement system disclosed in the Goldberg et al application for obtaining a linear readout of the concentration of water in an ink-water mixture is shown in FIG. 1. (The term "water" as used herein refers to any dampening solution used in conjunction with an ink; water is the greatest quantity of the dampener solution ingredients, but other additives such as buffering salts, acids, bases, gums, biocides and colorants may be contained in typical proprietary dampening mixtures.) FIG. 1 also represents a preferred system for implementing the present invention, which resides primarily in the provision of a specially designed capacitive cell that permits the testing of small, static samples of an ink mixture without the relatively large components and peripheral ink pumping and distribution equipment required in the Goldberg et al system.

The ink-water sample acts as a dielectric for a capacitor 2. The design of this capacitor, discussed in detail below, forms an important part of the present invention. Its capacitance depends upon the dielectric constant of the water-ink mixture, which in turn depends upon the concentration of water in the mixture.

Capacitor cell 2 is part of a circuit which forms an audio-frequency oscillator 4. The oscillator provides a square wave output signal over an output line 6, the frequency of the output signal being inversely proportional to the dielectric constant of the mixture in capacitor 2. A frequency to voltage converter 8 converts the output signal from oscillator 4 to a voltage on line 10, the voltage magnitude being exponentially related to the capacitance of cell 2. This voltage signal is converted to a base 10 logarithm by logarithmic amplifier 12. Because only a limited logarithmic range is required, amplifier 12 can be constructed from an inexpensive operational amplifier and an apppropriate npn transistor, or can be purchased as a modular unit. At low water concentrations (e.g., 0-20% water) the relationship between the water concentration and the dielectric constant is sufficiently linear to provide an accuracy of ±1% without a logarithmic amplifier. Consequently, for meters used only for measuring concentrations less than about 20% water, logarithmic amplifier 12 can be eliminated.

The output voltage produced by logarithmic amplifier 12 over line 14 or directly from line 10 for samples of sufficiently low water concentration is proportional to the concentration of water, offset by an arbitrary constant. This signal is applied to a signal conditioning amplifier 16, which has an adjustable offset voltage and an adjustable gain from 0.95 to 20. Amplifier 16 provides a zero voltage output when the concentration of water in the ink-water mixture is zero, and a value such as 5 volts when its concentration is 50%. The output of signal conditioner 16 is applied to a display device 18, which displays the mixture's water content as indicated by the value of the output from signal conditioner 16.

The preferred form of the invention uses concentric, coaxial electrodes spaced apart by an annular dielectric gap as the capacitive element. Other configurations could be used, such as two or more parallel plates. However, concentric electrodes achieve a greater amount of capacitance per unit volume of the entire cell, offer a more effective use of surface area, and a more reproducible positioning of the electrodes than other configurations. Also, parallel plate capacitance cells can suffer from drift problems, and using more than two plates can add significantly to the cost of the device.

The inner electrode 20 of a concentric cell is shown in FIG. 2. Electrode 20 has generally cylindrical side walls 22, and a closed bottom wall 24 which flares somewhat downward toward its center from the edges of side wall 22. The electrode is formed from a conductive material, such as solid aluminum, and includes a thin insulative coating 26 around its cylindrical periphery. Insulative coating 26 is preferably formed from a polymer such as 0.001 to 0.005 inch thick Teflon R; the width of the coating is somewhat exaggerated in the accompanying figures for purposes of clarity. A threaded positioning post 28 extends axially downward from the bottom of the electrode to position the electrode within the overall capacitive cell. A spacer ring 30 formed from a plastic or other insulating material is located over the top and upper sides of the electrode. A post 32, which is either formed integrally with the electrode or is electrically connected thereto, extends axially upward from the electrode to facilitate its handling during assembly and disassembly of the capacitor cell, and to contain a convenient electrical connector 33 (see FIG. 4) for the remainder of the oscillator circuit.

Referring now to FIG. 3, a preferred form of the outer electrode 34 is shown. This electrode is formed from a conductive material such as aluminum in the shape of a hollow cylinder, the inner diameter of which is somewhat greater than the outer diameter of the inner electrode. The inner surface of electrode 34 is provided with a thin insulative coating 36, such as the 0.002 inch Teflon R coating used for the inner electrode. An interior recess 38 is formed at the lower end of the electrode to accommodate an insulative base member in the form of a plastic plug 40. This element fits tightly wihin recess 38 to plug the bottom of the electrode and prevent any liquid from leaking out. It also includes a central threaded bore 42 which opens to the interior of electrode 34, when the plug is in place, to receive extenion post 28 of the inner electrode 20.

A lower cap 44 is provided with interior threading that mates with threading on the lower outer surface of outer electrode 34, enabling the cap to be screwed onto the bottom of the electrode and hold plug 40 in place. Cap 44 is formed from a metal or other conductive material and, in addition to securing plug 40 in place, contains the electrical field which is present when the device is used, thereby substantially preventing stray electrical fields from interfering with the measurement obtained by the device. A similar conductive cap 46 is adapted to be threaded over the upper end of outer electrode 34. The upper cap serves a similar function to lower cap 44 in containing electrical fields. A central insulating bushing 48 extends through the upper cap, enabling an electrical connection to be made with the inner electrode connector 33 from a location outside the cell. A connection means 50 such as a screw is also provided in the upper cap 46 to make an electrical connection with the outer electrode 34 through its electrical contact with the cap.

The assembled device is shown in FIG. 4, with inner electrode 20 located inside and coaxial with outer electrode 34. The lower post 28 extending from inner electrode 20 is screwed into threaded bore 42 in the insulating block 40, securing the inner electrode in its proper position. Lower cap 44 is screwed on over the bottom of outer electrode 34, thereby retaining block 40 in place, while upper cap 46 is screwed on over the top of the outer electrode to complete the electrical shield. The insulating spacer 30 extends around the upper surface of the inner electrode 20 to prevent it from accidentally contacting the outer electrode 34. Leads 52, 54 respectively make contact with the inner and outer electrodes (contact with the outer electrode is made via upper cap 46).

A fluid mixture 56 of ink and water can be contained in the gap between the inner and outer electrodes. The device thus comprises a capacitor cell, the capacitance of which is determined by the dielectric constant of the ink-water mixture and the dimensions of the various components. For repeatable and accurate measurements, it is desirable that the cell have a relatively high capacitance in the range of about 100 picofarads when empty. For convenience, it is desirable that the required volume of ink-water sample be not more than about 50 cc. In the embodiment shown in FIGS. 2–4, these specifications can be achieved with an inner electrode 20 which has a diameter of 2.375 inches and a cylinder height of 3.5 inches, and an outer electrode 34 with an inner diameter of 2.5 inches and a height of 4.0 inches above the plug recess.

At the relatively low operating frequency contemplated for the measuring device, typically about 9 kHz, electrolysis may result for fluid samples containing a high water content. Electrolysis spoils the reading obtained from the device, and should be avoided. The provision of the thin polymer coatings 26 and 36 on the opposed surfaces of the two electrodes effectively prevents electrolysis. The coatings are preferably in the range of 0.001–0.005 inches, which is thin enough to prevent the coatings from having any significant effect on the overall capacitance of the cell. The presence of the coatings also prevents enhanced capacitance due to double layer effects, characterized by a build-up of successive layers of ions of alterating polarity on each electrode, and resulting in a large error in the cell's reproducibility and capacitance.

In use, the sensing circuit depicted in FIG. 1 would be "zeroed" with the capacitive cell assembled but void of ink. To measure the water content of an ink sample, the inner electrode 20 is removed and a heavy-bodied sample of an ink mixture placed within the chamber formed by the outer electrode 34 and plug 40. The inner electrode is then replaced by threading post 28 into bore 42, displacing the ink mixture from the bottom of the chamber and forcing it to uniformly fill the gap between the opposed electrode surfaces. Any excess ink simply accumulates in the cavity 41 provided in the upper portions of the assembled device, and the upper cap 46 is threaded over the outer electrode to complete the assembly. The ink sample need not be measured precisely ahead of time because of this overflow accumulation feature, the coaxial portion of he device being the only portion electrically sensitive to the presence of ink. The device is small and portable, and requires no peripheral equipment or attachments such as ink pumps or ink distribution systems. For these reasons it is also quite inexpensive. The system can be used in the laboratory, or at various locations in an ink manufactuing or printing plant. Small ink samples can be conveniently collected from a number of different locations, such as the printing press rollers, during operation.

An alternate embodiment of the invention, which facilitates quicker and even more convenient water content measurements, is shown in FIG. 5. A frame assembly 58 includes a lower base 60 which encloses the system electronics and supports an outer electrode 62, and an upper structure which includes a crank system 64 for raising and lowering an inner electrode 66. The dimensions of electrodes 62 and 66 are similar to those of the inner and outer electrodes shown in FIGS. 2–4. The inner electrode 66 fits inside the outer electrode 62 and is separated therefrom about its periphery by a gap. The gap can be filled with an ink-water mixture to produce a capacitive cell with a capacitance equivalent to that of the FIGS. 2–4 embodiment. The outer electrode 62 is basically in the form of a cylindrical metal cup, and is permanently attached in a fixed position to the frame assembly base 60. The inner electrode 66 includes an elongate shaft 68 which extends vertically upward and is engaged by the crank assembly 64, such that the shaft and inner eectrode can be raised or lowered as desired by operating the crank assembly. An upper cap 70 is adapted to be placed over the top of outer electode 62 when the inner electrode 66 is moved to its lowest position, thereby electrically sealing the cell.

The outer surface of inner electrode 66 and the inner surface of outer electrode 62 are both provided with insulative polymer coatings or layers, as in the previous embodiment. Preferably, however, the insulative layers are in the form of thin plastic liners 72 and 74 that are configured to abut the inner surface of outer electrode 62, and the outer surface of inner electrode 66, respectively. The liners 72 and 74 can be easily removed from their respective electrodes, thereby making possible the quick removal of ink left from a sample without having to clean the electrodes themselves. The liners are disposable, and a new pair is put in place before testing another ink sample.

The electronic circuitry is preferably housed within the base 60 of the frame assembly. Appropriate electrical connections (not shown in FIG. 5) are provided between the circuitry and the two electrodes.

A functional schematic diagram of electrical circuitry that could be used in conjunction with either of the embodiments described above is shown in FIG. 6. The oscillator (multi-vibrator) 10 of FIG. 1 is shown at the upper left hand corner of FIG. 6, and includes an amplifier A1. A three-position switch is used to select the appropriate feedback capacitors to set the frequency for a particular reference point, such as the frequency produced when the capacitive cell is empty or filled with a known ink-water mixture. The output from the osillator is amplified in amplifier A2 by an amount determined by the positive gain setting $(50+2)/x$, where x is the resistance between the wiper of the 50 kOhm potentiometer and ground. This is a non-critical setting, and is needed only to ensure a proper signal amplitude to trigger a frequency-to-voltage converter, shown in the lower right corner of the figure. This latter integrated circuit, which may be a Burr-Brown VF32, provides a voltage directly proporional to the input frequency. A reference voltage to input 1 provides a reference to the logarithmic zero point.

This constant voltage is fed into a logarithmic amplifier, such as a Burr-Brown Log 100 module, shown at the bottom center of FIG. 6. The amplifier is connected such that a three-decade span per ten volts is maintained. A reference current to pin 14 is supplied by a simple current regulated circuit shown below the log-amplifier. The output of the unit is positive above a 1 volt input (log 1=0), and is inverted by the zero to 31 1 gain amplifier A4. The gain settings are switched with the appropriate feedback resistors for the multivibrator circuit, as shown by the dotted line. Amplifier A4 serves two functions. The first is to establish the proportionality constant between output voltage and water content, using the appropriate gain settings as described above. The second is to establish a zero reference voltage to correct for the offset in the relationship between voltage and water content.

The output of A4 is fed into another amplifier A3, which acts as a buffer for a digital panel meter DM 3100L set for a 0 to 5 volt output. This unit can be adjusted, for example, to produce a 1 volt reading for a 10% water concentration. The four amplifiers (A1–A4) shown in FIG. 6 can be combined into a "quad op-amp" integrated circuit such as the National Semiconductor LF 457.

With nominal modifications the circuit can be adjusted to operate at any frequency which responds linearly to the dielectric constant of the ink mixture. Frequencies which can be used for various inks range from less than 4 kHz to over 300 kHz. However, care should be taken in the construction of the measurement device to minimize stray capacitance, and to use an amplifier with a sufficient gain-bandwidth product and a negligible phase shift below 3 MHz.

Alternate embodiments of an inexpensive device for performing static measurements of small samples of an ink mixture have thus been shown and described. As numerous modifications and additional embodiments will occur to those skilled in the art, it is intended that the invention be limited only in terms of the appended claims.

What is claimed is:

1. A device for measuring the water content of a non-flowing fluid mixture of ink and water, the dielectric constant of the fluid mixture varying with its water content, comprising:
   (a) a capacitor cell comprising:
      (1) first and second electrodes, wherein the first electrode is disposed inward of the second electrode and has an outer surface which is spaced from the inner surface of the second electrode,
      (2) means for positioning the electrodes with their respective surfaces mutually opposed and separated by a predetermined gap,
      (3) means for containing a fluid mixture in the gap between the electrodes, and
      (4) an insulative base for the first and second electrodes, the first electrode being movable away from the base to enable the introduction of a fluid mixture into the space defined by the base and second electrode, and movable back to a fixed position against the base so that at least part of the fluid mixture is displaced into the gap between the first and second electrodes,
   (b) an oscillator circuit which includes said capacitor cell, the oscillator circuit providing an output signal with a frequency that varies in a known manner with the dielectric constant of the fluid mixture, and
   (c) an output means connected to provide an output display which varies with the output signal frequency, and thereby indicates the concentration of water in the fluid mixture.

2. The device of claim 1, the outer surface of the first electrode and the inner surface of the second electrode being substantially cylindrical and coaxial.

3. The device of claim 1, further including thin layers of insulative material on the mutually opposed electrode surfaces to impede electrolysis and double layer capacitive effects, the layers being removable from their respective electrodes to facilitate cleaning of the measuring device.

4. A device for measuring the water content of a static fluid mixture of ink and water, the dielectric constant of the fluid mixture varying with its water content, comprising:
   an inner electrode having a generally cylindrical outer surface,
   an outer electrode having a generally cylindrical inner surface the diameter of which is greater than the diameter of the inner electrode's outer surface,
   means for positioning the inner electrode substantially coaxially inward of the outer electrode,
   means for containing a static amount of fluid mixture in the gap between the outer surface of the inner electrode and the inner surface of the outer electrode,
   an insultative blocking member blocking a lower end of the outer electrode to prevent the fluid mixture from flowing out that end, a corresponding lower end of the inner electrode being closed and adapted to be seated against the blocking member when the inner electrode is placed in a vertical operative position inward of the outer electrode, and the inner electrode being removable from its operative position to permit the introduction of a fluid mixture into the interior of the outer electrode, and replaceable to its operative position to displace the fluid mixture into substantially the entire gap between the two electrodes when a sufficient quantity of the fluid mixture has been introduced,
   an oscillator circuit which includes the electrodes and the fluid mixture therein as a capacitive element, the oscillator circuit providing an output signal with a frequency that varies in a known manner with the dielectric constant of the fluid, and
   an output means connected to provide an output display which varies with the output signal frequency, and thereby indicates the concentration of water in the fluid mixture.

5. The device of claim 4, the blocking member including a centrally located threaded opening, and the inner electrode including a threaded extension which is adapted to be threaded into the opening to position the inner electrode in an operative position.

6. The device of claim 4, further comprising a lower conductive cap adapted to be positioned over the blocking member and the lower end of the outer electrode, and an upper conductive cap adapted to be positioned over upper ends of the inner and outer electrodes, the caps serving to contain stray electric fields.

7. The device of claim 6, further comprising an insulative spacer member positioned over the upper end of the inner electrode to insulate it from the outer electrode.

8. The device of claim 4, further comprising thin layers of insulative material on the mutually opposed surfaces of the inner and outer electrodes to impede electrolysis and double layer effects, the layers being removable to facilitate cleaning of the measuring device.

9. A device for measuring the water content of a static fluid mixture of ink and water, the dielectric constant of the fluid mixture varying with its water content, comprising:

an inner electrode having a generally cylindrical outer surface and a closed lower end;

an outer electrode having a generally cylindrical inner surface the diameter of which is greater than the diameter of the inner electrode's outer surface, and having a closed lower end and an open upper end, the lower portion of at least one of the inner and outer electrodes including an insulating material insulating the two electrodes from each other;

a frame assembly securing the outer electrode in a fixed position with its open end facing up;

an elongated shaft extending upward from the inner electrode;

a means on the frame assembly engaging the shaft to lower the inner electrode to an operative position coaxially inward of the outer electrode and to raise the inner electrode up from its operative position to enable the introduction of the fluid mixture into the outer electrode;

an oscillator circuit which includes the electrodes and the fluid mixture therein as a capacitive element, the oscillator circuit providing an output signal with a frequency that varies in a known manner with the dielectric constant of the fluid; and an output means connected to provide an output display which varies with the output signal frequency, and thereby indicates the concentration of water in the fluid mixture.

10. The device of claim 9, the closed lower end of the outer electrode being formed from a conductive material, and further comprising a conductive cap adapted to be placed over the upper ends of the electrodes to contain stray electric fields.

11. The device of claim 9, further comprising thin layers of insulative material on the mutually opposed surfaces of the inner and outer electrodes to impede electrolysis and double layer effects, the layers being removable to facilitate cleaning of the measuring device.

* * * * *